US011051739B2

(12) United States Patent
Kozhaya et al.

(10) Patent No.: US 11,051,739 B2
(45) Date of Patent: Jul. 6, 2021

(54) NEURAL MAPPING

(71) Applicant: INTERNATIONAL BUSINESS MACHINES CORPORATION, Armonk, NY (US)

(72) Inventors: Joseph N. Kozhaya, Morrisville, NC (US); Ryan R. Anderson, Kensington, CA (US); Rama Kalyani T. Akkiraju, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 903 days.

(21) Appl. No.: 15/716,565

(22) Filed: Sep. 27, 2017

(65) Prior Publication Data

US 2019/0090771 A1    Mar. 28, 2019

(51) Int. Cl.
| A61B 5/316 | (2021.01) |
| A61B 5/00 | (2006.01) |
| A61B 5/16 | (2006.01) |
| G06F 17/18 | (2006.01) |
| G16H 20/00 | (2018.01) |
| G16H 40/67 | (2018.01) |
| A61B 5/1455 | (2006.01) |
| G16H 50/70 | (2018.01) |

(Continued)

(52) U.S. Cl.
CPC .......... *A61B 5/316* (2021.01); *A61B 5/14553* (2013.01); *A61B 5/165* (2013.01); *A61B 5/369* (2021.01); *A61B 5/38* (2021.01); *A61B 5/7267* (2013.01); *G06F 17/18* (2013.01); *G16H 20/00* (2018.01); *G16H 40/67* (2018.01); *G16H 50/20* (2018.01); *G16H 50/70* (2018.01); *A61B 5/4824* (2013.01); *G16H 50/50* (2018.01)

(58) Field of Classification Search
CPC . A61B 5/38; A61B 5/7267; A61B 5/377–383; G16H 50/70
See application file for complete search history.

(56) References Cited

U.S. PATENT DOCUMENTS

| 2005/0177058 A1 | 8/2005 | Sobell |
| 2014/0214730 A9 | 7/2014 | Shahaf et al. |

(Continued)

OTHER PUBLICATIONS

IBM: List of IBM Patents or Patent Applications Treated as Related (Appendix P), Dec. 28, 2017, pp. 1-2.

(Continued)

*Primary Examiner* — Amar Movva
(74) *Attorney, Agent, or Firm* — Anthony R. Curro

(57) ABSTRACT

An embodiment of the invention may include a method, computer program product and computer system for neural activity interpretation. The method, computer program product and computer system may include a computing device that presents a first user with a stimulus and monitors and maps the neural activity of the first user. The computing device may receive the first user's verbal reaction to the stimulus and map the linguistic data of the first user's verbal reaction to form a high dimensional vector based on the relationships of the mapped neural activity and the mapped verbal reaction of the first user. The computing device may associate the high dimensional vector with the stimulus presented resulting in a thoughts model. The computing device may receive a second user's neural activity and compare that second user's neural activity to the thoughts model to identify the neural activity in the second user.

11 Claims, 6 Drawing Sheets

(51) Int. Cl.
*G16H 50/20* (2018.01)
*A61B 5/369* (2021.01)
*A61B 5/38* (2021.01)
*G16H 50/50* (2018.01)

(56) References Cited

U.S. PATENT DOCUMENTS

2015/0305685 A1  10/2015  Shahaf et al.
2016/0058392 A1  3/2016   Hasson et al.
2017/0065229 A1  3/2017   Howard
2019/0090772 A1  3/2019   Kozhaya

OTHER PUBLICATIONS

Pending U.S. Appl. No. 15/816,193, filed Nov. 17, 2017, entitled: "Predicting Thought Baser on Neural Mapping", pp. 1-28.
Pennington et al., "GloVe: Global Vectors for Word Representation", Proceedings of the 2014 Conference on Empirical Methods in Natural Language Processing (EMNLP), Oct. 25-29, 2014, pp. 1532-1543, Copyright 2014 Association for Computational Linguistics, Doha, Qatar.
Wikipedia, "Human Brain", Printed on Sep. 21, 2017, 36 pages, http://en.wikipedia.org/wiki/Human_brain.
Neuroscape, "Technology", Printed on Sep. 21, 2017, 14 pages, http://neuroscape.uscf.edu/technology/#glass-brain.
Isaacson, "A Fitbit for Your Brain Is Around the Corner", Newsweek, Apr. 3, 2016, 10 Pages, http://www.newsweek.com/2016/04/15/human-brain-eeg-technology.
Mell et al., "The NIST Definition of Cloud Computing", NIST, Sep. 2011, 7 Pages, Special Publication 800-145, U.S. Department of Commerce, Gaithersburg, MD.
Mullen, "SIFT: Welcome to the repository for the Source Information Flow Toolbox", Printed on Sep. 26, 2017, 6 Pages, http://sccn.uscd.edu/wiki/SIFT.
Scutti, "Brain Cartography: Modern-Day Explorers Are Mapping the Wiring of the Human Mind", Newsweek, Apr. 25, 2016, 11 Pages, Brain Issue 2016, Newsweek LLC.
Kothe et al., "BCILAB: Open Source Matlab Toolbox for Brain-Computer Interface Research", SCCN, Printed on Sep. 26, 2017, 38 Pages, https://sccn.ucsd.edu/wiki/BCILAB.
Neuroscape Lab, "Bridging the Gap Between Technology and Neuroscience," Neuroscape Lab Datasheet [online][accessed on Feb. 18, 2021], 3 pages, Retrieved from the Internet: <URL: https://web.archive.org/Web/20161006152338/http://neuroscapelab.com/>.
Neuroscape Lab, "Glass Brain," Neuroscape Lab Datasheet [online], [accessed on Feb. 18, 2021], 2 pages, Retrieved from the Internet: <URL: https://web.archive.org/web/20161010001821/http://neuroscapelab.com/projects/glass-brain>.
Neuroscape Lab, "Projects," Neuroscape Lab Datasheet [online], [accessed on Feb. 18, 201], 3 pp., Retrieved from the Internet: <URL: https://web.archive.org/web/20161004234826/http://neuroscapelab.com/projects/>.

NEURAL MAPPING

BACKGROUND

The present invention relates generally to a method, system, and computer program for the prediction of human thought based on neural activity. More particularly, the present invention relates to a method, system, and computer program for mapping neural activity and user data to a high-dimensional vector enabling thought prediction.

Neural mapping is a process that maps neural activity, e.g. from an electroencephalogram (EEG), or other neuroimaging devices such as a functional near-infrared spectroscopy (fNIRS), to depict visual representations, e.g. maps, of real-time brain activity. Neural mapping thus enables the visualization of active neural areas associated with a cognitive action such as a thought or memory.

BRIEF SUMMARY

An embodiment of the invention may include a method, computer program product and computer system for neural activity interpretation. The method, computer program product and computer system may include a computing device that presents a first user with a stimulus and monitors and maps the neural activity of the first user. The computing device may receive the first user's verbal reaction to the stimulus and map the linguistic data of the first user's verbal reaction to form a high dimensional vector based on the relationships of the mapped neural activity of the first user and the mapped verbal reaction of the first user. The computing device may associate the high dimensional vector with the stimulus presented resulting in a thoughts model. The computing device may receive a second user's neural activity and compare that second user's neural activity to the thoughts model to identify the neural activity in the second user.

The computing device may use the thoughts model to compare and identify similar neural activity in a second user.

DETAILED DESCRIPTION

Embodiments of the present invention will now be described in detail with reference to the accompanying Figures.

Figure 1:
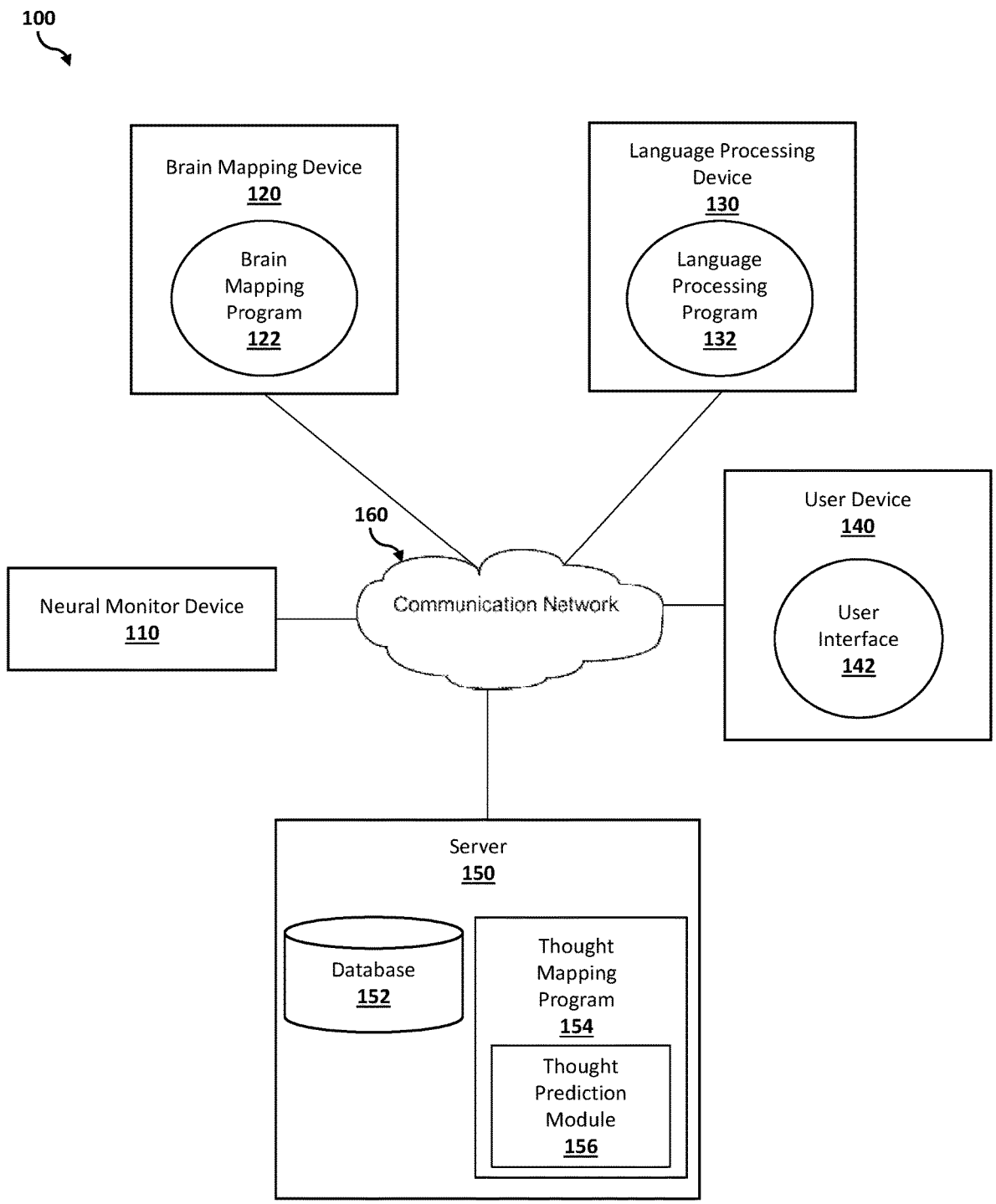
FIG. 1 illustrates a system for thought prediction from neural activity, in accordance with an embodiment of the invention.

FIG. 1 illustrates a thought prediction system 100, in accordance with an embodiment of the invention. In an example embodiment, thought prediction system 100 includes neural monitor device 110, brain mapping device 120, language processing device 130, user device 140, and server 150 interconnected via network 160.

In the example embodiment, network 160 is the Internet, representing a worldwide collection of networks and gateways to support communications between devices connected to the Internet. Network 160 may include, for example, wired, wireless or fiber optic connections. In other embodiments, network 160 may be implemented as an intranet, a local area network (LAN), or a wide area network (WAN). In general, network 160 can be any combination of connections and protocols that will support communications between neural monitor device 110, brain mapping device 120, language processing device 130, user device 140, and server 150.

Neural monitor device 110 may be an electroencephalogram (EEG) or any electrophysiological device capable of detecting neural activity. In an example embodiment, neural monitor device 110 may be a high-density EEG. For example, neural monitor device 110 may be an Emotiv® wireless EEG headset such as the Emotiv® Insight or Epoc+ EEG devices (Emotiv is a registered trademark of Emotiv, LLC). In another embodiment, neural monitor device 110 may be a functional near-infrared spectroscopy (fNIRS) or any neuroimaging device. For example, neural monitor device 110 may be a Hitachi® ETG 4000, a NIRx NIRSport Tandem, or a NIRx NIRScout (HITACHI is a registered trademark of Hitachi, Ltd.).

Brain mapping device 120 may be any device capable of receiving and displaying neural activity signal input from neural monitor device 110 via network 160. Brain mapping device 120 may be a desktop computer, a notebook, a laptop computer, a tablet computer, a handheld device, a smart-phone, a cellular phone, a television, or any other electronic device, computing system, wired or wireless device capable of receiving and sending content to and from other computing devices, such as neural monitor device 110, language processing device 130, user device 140, and server 150, via network 160. Brain Mapping device 120 may include brain mapping program 122.

Brain mapping program 122 may include components to receive neural activity input from neural monitor device 110 and process the neural activity input to depict visual representations, e.g. maps, of real-time brain activity. In an example embodiment, brain mapping program 122 may be Emotiv's® MyEMOTIV or Pure EEG software. In an alternative embodiment, brain mapping program 122 may be Glass Brain, a Unity3D brain visualization that displays source activity and connectivity, inferred in real-time from high-density EEG using methods implemented in Source Information Flow Toolbox (SIFT) and BCILAB, a brain-computer interface toolbox, developed by University of California San Diego (UCSD®) and University of California San Francisco (UCSF®) (UCSD and UCSF are trademarks of The Regents of the University of California Corp.). While the above systems may be used, brain mapping program 122 may be any brain-computer program capable of receiving neural activity, input, e.g. from an EEG or fNIRS device, and processing that input to depict visualization of brain activity.

Language processing device 130 may be any device capable of language processing and may include language processing program 132. Language processing device 130 may be a desktop computer, a notebook, a laptop computer, a tablet computer, a handheld device, a smart-phone, a cellular phone, a landline phone, a thin client, or any other electronic device, computing system, wired or wireless device capable of receiving and sending user input to and from other computing devices, such as neural monitor device 110, brain mapping device 120, user device 140, and server 150, via network 160. In an example embodiment, language processing device 130 may be IBM® Watson™ (IBM is a registered trademark of International Business Machines, Corp.; WATSON is a trademark of International Business Machines, Corp.).

Language processing program 132 may include components used to receive input from a user and transmit the input to thought mapping program 154 residing on server 150. In an example embodiment, language processing program 132 uses a combination of technologies and devices, such as device drivers, to process user input and send that processed input to server 150, via network 160. In the example embodiment, language processing program 132 receives input, such as audio input received from a user via a physical input device, such as a microphone. Language processing program 132 then processes the received input, which is described in more detail below. For example, language processing program 132 may include IBM's AlchemyLanguage application programming interfaces.

User device 140 may include user interface 142. User device 140 may be a desktop computer, a notebook, a laptop computer, a tablet computer, a handheld device, a smartphone, a cellular phone, a television, or any other electronic device, computing system, wired or wireless device capable of receiving and sending content to and from other computing devices, such as neural monitor device 110, brain mapping device 120, language processing device 130, and sever 150, via network 160. In an example embodiment, user device 140 may be a monitor screen capable of displaying visual and auditory stimuli stored on server 150 to a user. User device 140 may also include a physical input device, such as, but not limited to, a microphone. In an alternative embodiment, user device 140 may be a virtual reality device capable of communicating with neural monitor device 110, brain mapping device 120, language processing device 130, and server 150, via network 160.

User interface 142 may include components used to receive information from server 150 and display the information to the user, or conversely, to receive input from a user and transmit the input to brain mapping device 120, language processing device 130, and/or server 150. In an example embodiment, user interface 142 uses a combination of technologies and devices, such as device drivers or virtual reality, to provide visual and/or auditory stimuli to a user and enable users of user device 140 to interact with thought prediction system 100.

Server 150 includes database 152, and thought mapping program 154, which may include thought prediction module 156. In the example embodiment, server 150 may be a desktop computer, a notebook, a laptop computer, a tablet computer, a thin client, or any other electronic device or computing system capable of storing compiling and organizing audio, visual, textual, or neural activity content and receiving and sending that content to and from other computing devices, such as neural monitor device 110, brain mapping device 120, language processing device 130, and user device 140, via network 160.

Database 152 is a collection of data obtained from neural monitor device 110, brain mapping device 120, language processing device 130, user device 140, and thought mapping program 154. The data stored on database 152 may include, but is not limited to, neural activity received from neural monitor device 110, brain maps received from brain mapping device 120, processed language data received from language processing device 130, user data received from user device 140, and mapped data from thought mapping program 154. Additionally, database 152 may also contain stimulus files such as visual or auditory stimuli for output to user device 140. Database 152 may also contain user attribute data, such as, but not limited to, the user's age, gender, and language spoken, which may be input directly into server 150. Database 152 may also contain indexing information about the relationship between the neural activity detected by neural monitor device 110, brain maps received from brain mapping device 120, processed language data received from language processing device 130, and user data received from user device 140.

Thought mapping program 154 is a program capable of mapping neural activity signals to a vector based on input received from one or all of neural monitor device 110, brain mapping device 120, language processing device 130, or user device 140. Thought mapping program 154 may include thought prediction module 156.

Thought prediction module 156 is a module capable predicting a user's thoughts based on input received from one or all of neural monitor device 110, brain mapping device 120, language processing device 130, or user device 140 and processed by thought mapping program 154.

Figure 2:
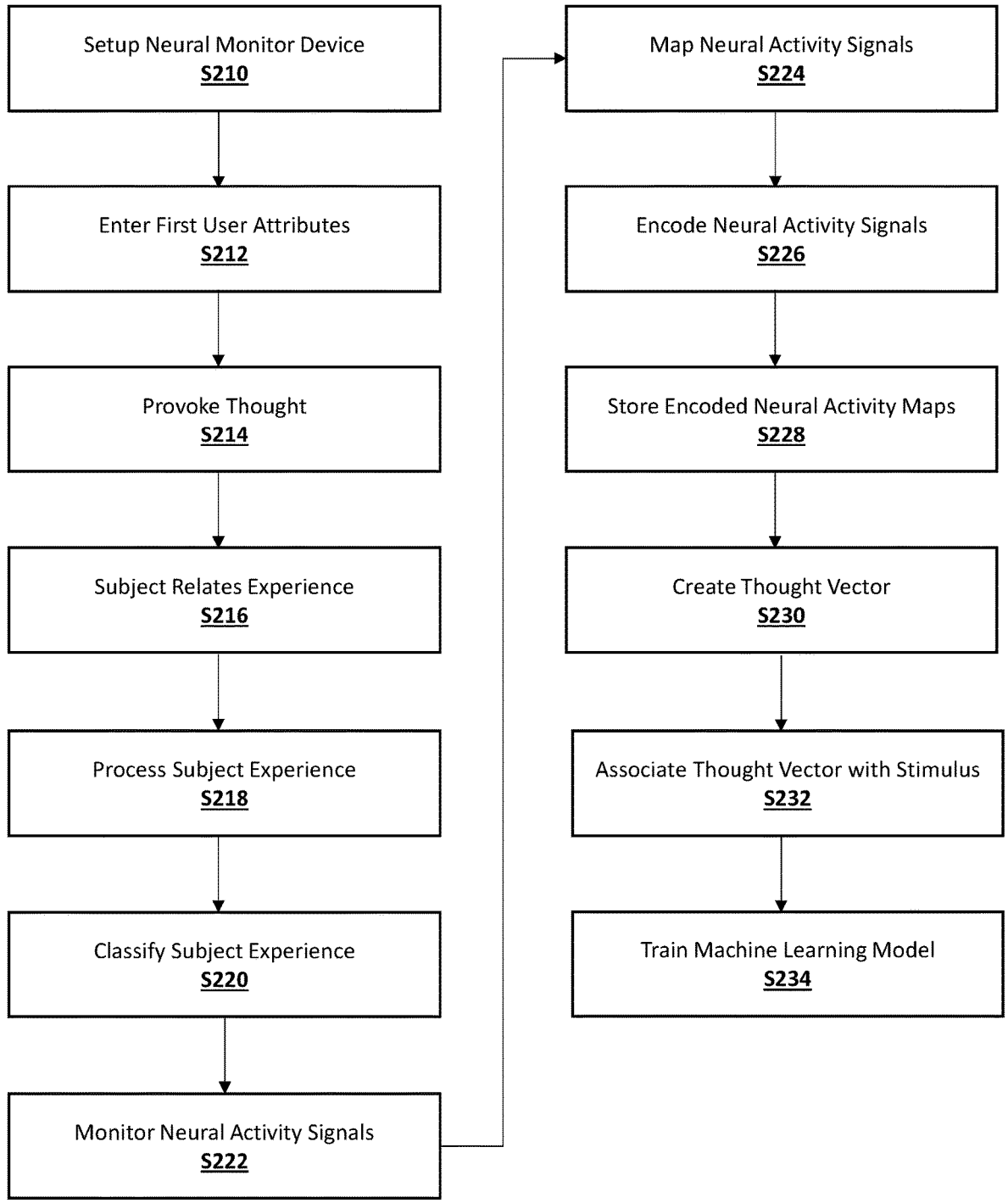
FIG. 2 is a flowchart illustrating a method for mapping neural activity of verbally communicative first users into a high-dimensional vector, in accordance with an embodiment of the invention.

FIG. 2 is a flowchart illustrating a method for mapping neural activity of verbally communicative users into a high-dimensional vector, in accordance with an embodiment of the invention.

Referring to step S210, a first user is connected to neural monitor device 110 by a professional. The first user's attributes are then entered into server 150 by a professional at step S212. The relevant first user attributes to be entered may include, but are not limited to, the first user's age, gender, and/or languages spoken. In an example embodiment, the first user is a person who is capable of verbal communication.

Referring to step S214, a stimulus is presented to a first user via user device 140 to provoke a thought in the first user. The stimulus may be, but is not limited to, visual, auditory, sensory, mechanical, and/or chemical in nature. The stimulus may be tailored to elicit a specific type of emotional response in a first user; e.g. sadness, anger, happiness, sympathy, etc. Further, the stimulus may be tailored to elicit a specific memory, trigger a specific sense, such as vision, hearing, touch, smell, taste, trigger a specific cognitive state, such as learning, confused, comprehending, trigger a specific psychological response or brain region, or trigger a first user's judgement. In an alternative embodiment, the stimulus presented to the first user may be done manually by a professional such as through spoken language or presenting a physical image.

Referring to step S216, a first user verbally relates details about their experience in response to the stimulus via user device 140. The details to be related by the first user may include, but are not limited to, emotional state of the first user, memories of the first user, senses experienced by the first user, and/or the cognitive state of the first user.

Referring to step S218 language processing device 130 maps the first user's verbal input creating a thought output. The thought output created by language processing device 130 and language processing program 132 may be, but is not limited to one or a combination of, a transcription of the first user's verbal input, a word map of the first user's verbal input, a topic map of the first user's verbal input, an emotion map of the first user's verbal input, or a time map of the first user's verbal input. In an example embodiment, language processing program 132 may use a variety of word embedding methods and algorithms to create the word maps including, but not limited to, word2vec and Global Vectors for Word Representation (GloVe) to embed the thought output into vectors of real numbers to be used in matrix M. Word2vec may utilize either continuous bag-of-words (CBOW) architecture model or continuous skip-gram (C-SG) model architecture to embed the recorded user data. CBOW enables the prediction of a word based its surrounding words. C-SG enables the prediction of surrounding words based on a single word.

Referring to step S220 language processing device 130 classifies the first user's verbal input as a specific type of thought, e.g. sadness, anger, happiness, sympathy, etc., based on the thought output. It may be appreciated that the first users' verbal input may be classified as more than one type of specific thought. Further, the first users' verbal input may be classified based on, but not limited to the first user's tone, emotion, or education. In an example embodiment, language processing device 130 may use out-of-box application programming interfaces (APIs) to classify the first user's verbal input such as, but not limited to, IBM® Watson's TONE or NLU interfaces. In another example embodiment, language processing device 130 may use a custom trained natural language classifier (NLC).

Referring to step S222-S224 a first user's neural activity is monitored and mapped using brain mapping device 120. A user's neural activity may be visualized and mapped using brain mapping program 122.

Referring to step S226, server 150 receives the neural activity maps of the first user, via network 160, and thought mapping program 154 encodes the neural activity signals of the neural activity maps of the first user. There are several ways in which the neural activity signals may be encoded. In an example embodiment, neural activity signals may be encoded using a binary system. In a binary system, brain mapping device 120 detects neural activity signal intensity and thought mapping program 154 encodes the signals with an average intensity above a set threshold as a 1 and signals with an average intensity below that set threshold as a 0. In another embodiment, neural activity signals may be encoded as a value using actual metrics of the signals themselves, such as, average intensity or maximum intensity. In yet another embodiment, neural activity signals may be encoded using a derived metric of the signals, such as the Fourier Transform that describes the frequency of the signals.

Referring to step S228, server 150 stores the encoded neural activity maps on database 152.

Referring to step S230, thought mapping program 154 forms a thought vector using the encoded first user's neural activity signals, thought output, and stored first user attributes. For example, thought mapping program 154 would create matrix M, which may have rows corresponding, but not limited to, a specific thought, memory, sense, cognitive state, etc. and columns corresponding to a single encoded neural activity signal that related to the specific thought, memory, sense, cognitive state, etc. Thus, thought mapping program 154 creates a multi-dimensional array, i.e. a thought vector, consisting of the encoded first user's neural activity signals, thought output, and stored user attributes for a single thought. This thought vector may be expressed with each thought (T) as a function of all associated neural activity signals $(S_1, S_2, S_3, S_4 \ldots S_n)$, i.e. $T=fn(S_1, S_2, S_3, S_4 \ldots S_n)$.

Referring to Step 232, thought mapping program 154 associates the thought vector with the stimulus presented to the first user at step S214.

Steps S210-S232 may be repeated for a number first users, all capable of verbal communication, and number of different specific thoughts memory, sense, cognitive state, etc.

Referring to step S234, thought mapping program 154 trains machine learning models using all thought vectors created in steps S210-S232, creating thought prediction module 156. Any known machine learning algorithm may be used including, but not limited to, Support Vector Machines, or Nave Bayesian. In another embodiment, neural networks may be used to build thought prediction modules.

Figure 3:
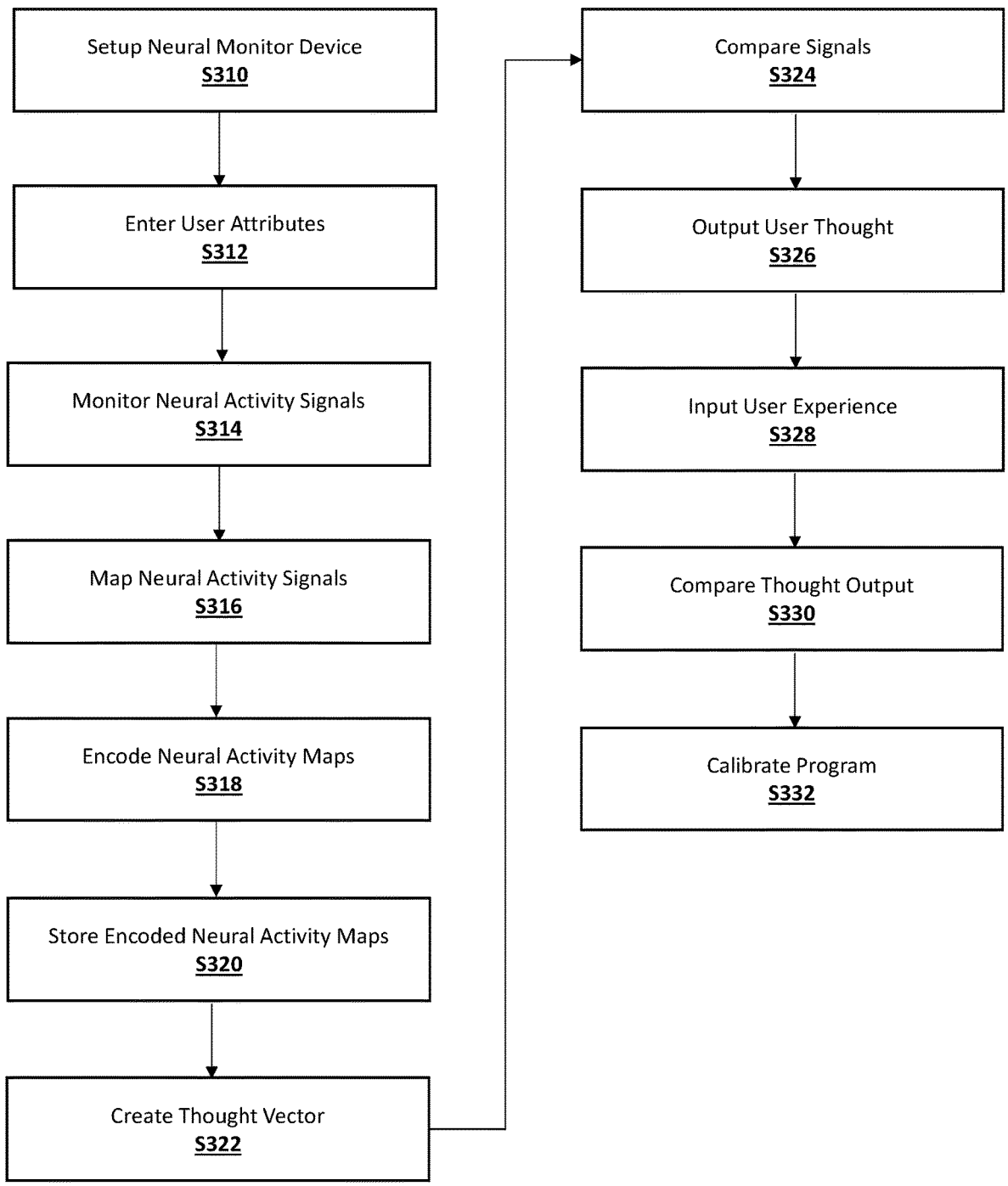
FIG. 3 is a flowchart illustrating a method for predicting thoughts of a second user based on neural activity.

FIG. 3 is a flowchart illustrating a method for predicting a second user's thoughts based on a second user's neural activity, in accordance with an embodiment of the invention.

Referring to FIG. 3, steps S310-S312 are the same as steps S210-S212, and steps S314-S322 are the same steps S222-S230 above, but for a second user. In an example embodiment, the second user is a person who was not previously used to train thought prediction system 100 as described above in steps S210-S234. Further, the second user may be non-verbal, or otherwise unable to effectively communicate verbally. In another embodiment, the second user may be the same as the first user, but who has deteriorated, or is deteriorating, mentally since training thought prediction system 100, such as, but not limited to, an Alzheimer's patient. A second user is connected to a neural monitor device 110 and the user's attributes are then entered into server 150 by a professional. The second user's neural activity is monitored and mapped using brain mapping device 120. Server 150 receives the neural activity maps, via network 160. Thought mapping program 154 encodes the neural activity signals of the neural activity maps and then stores the encoded neural activity maps on database 152. Thought mapping program 154 maps the encoded neural activity signals to thought vectors.

Referring to step S324, thought prediction module 156 then compares the encoded neural activity signals of the second user with all mapped thoughts of the first users. For example, a speech challenged person who needs to communicate can express a thought and neural monitor device 110 and brain mapping device 120 monitors and maps the neural activity signals of the speech challenged person to a vector space as described in detail above. The mapped neural activity signals of the speech challenged person are then compared to the previously created thought vectors of the first users and the most similar one(s) is/are identified.

Referring to step S326, thought prediction module 156 outputs the data associated with the identified first users' thought to an external device, such as but not limited to, user device 140. The output data may be, but it not limited to, audio, visual, or textual data. In the example above, the speech challenged person's caregiver, family member, or friend is then able to see or hear the speech challenged person's thoughts.

As indicated above, the second user may be non-verbal, or otherwise unable to effectively communicate verbally. However, it may be appreciated that the second user may be able to communicate fully or in a compromised fashion via means other than verbal communication, such as, writing, typing, or any other means of communication. If the second user is capable some form of communication, the inventive system may proceed through steps S328-S332 to calibrate the inventive system.

Referring to step S328 the second user may relate details about their thought via user device 140. The details to be related by the second user may include, but are not limited to, emotional state of the second user, memories of the second user, senses experienced by the second user, and/or the cognitive state of the second user.

Referring to step S330 thought mapping program 154 may compare the thought output data of step S326 to the input of the second user. Thought mapping program 154 may identify any similarities or differences between the thought output and the input of the second user. For example, at step 328 a second user may indicate a particular idea, thought, or moment. However, that patient's neural activity may not align with the vector typically associated with that particular idea, thought, or moment. Thus, the system will identify the differences in the average neural activity and the patient's unique neural activity.

Referring to the step S332 thought mapping program 154 calibrates the thought vectors for the second user based on the data comparison of step S330 for the second user. For example, the thought mapping program 154 may adjust the parameters of the thought vector of a particular idea, thought, or moment for the second user.

In another example use of the invention, a patient in a coma may be connected to neural monitor device 110. The coma patient's attributes are then entered into server 150 by a professional. The coma patient's neural activity is monitored and mapped using brain mapping device 120. Server 150 receives the neural activity maps of the coma patient, via network 160. Thought prediction module 156 encodes the neural activity signals of the neural activity maps of the coma patient stores the encoded neural activity maps on database 152 and maps the encoded neural activity signals to thought vectors. Thought prediction module 156 then compares the encoded neural activity signals of the coma patient with all mapped thoughts of the first users and identifies the most similar. Thought prediction module 156 then outputs a textual or verbal representation of the identified thoughts that most closely match those of the coma patient. Thus, a caregiver, family member, or friend can see what, if anything, the coma patient is thinking.

In yet another example use of this invention, the first user may be a patient who is in the early stages of Alzheimer's disease or has been identified as being at risk for Alzheimer's disease. Thought mapping program 154 would create thought vectors specific to the patient as outlined above in FIGS. 2-3. Then, once the patient's Alzheimer's has progressed, medical professionals, caregivers, family members, and friends would be able to use thought prediction system 100 to communicate with the patient on a system that has been specifically calibrated to that individual when he/she was healthy. Further, medical professionals would be able to use thought prediction system 100 to monitor the precise areas of deterioration of the patient's brain over time by comparing successive neural activity maps. Thus, thought prediction system 100 allows for more precise diagnosis and treatment of a patient with Alzheimer's disease.

Figure 4:
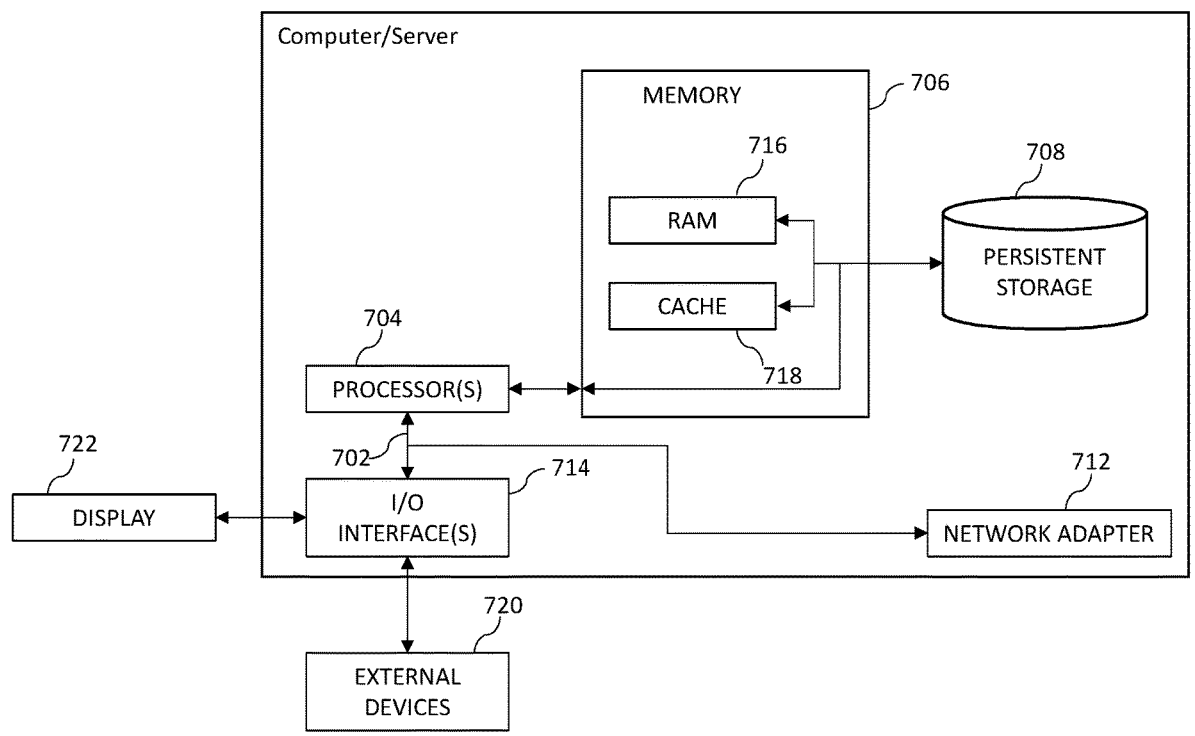
FIG. 4 is a block diagram depicting the hardware components of the thought prediction system of FIG. 1, in accordance with an embodiment of the invention.

FIG. 4 depicts a block diagram of components of server 150, neural monitor device 110, brain mapping device 120, language processing device 130, and user device 140, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Server 150, neural monitor device 110, brain mapping device 120, language processing device 130, and user device 140 may include communications fabric 702, which provides communications between computer processor(s) 704, memory 706, persistent storage 708, communications unit 712, and input/output (I/O) interface(s) 714. Communications fabric 702 can be implemented with any architecture designed for passing data and/or control information between processors (such as microprocessors, communications and network processors, etc.), system memory, peripheral devices, and any other hardware components within a system. For example, communications fabric 702 can be implemented with one or more buses.

Memory 706 and persistent storage 708 are computer-readable storage media. In this embodiment, memory 706 includes random access memory (RAM) 716 and cache memory 718. In general, memory 706 can include any suitable volatile or non-volatile computer-readable storage media.

The programs thought mapping program 154 in server 150, brain mapping program 122 in brain mapping device 120, language processing program 132 in language processing device 130, and user interface 142 stored in user device 140, are stored in persistent storage 708 for execution by one or more of the respective computer processors 704 via one or more memories of memory 706. In this embodiment, persistent storage 708 includes a magnetic hard disk drive. Alternatively, or in addition to a magnetic hard disk drive, persistent storage 708 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 708 may also be removable. For example, a removable hard drive may be used for persistent storage 708. Other examples include optical and magnetic disks, thumb drives, and smart cards that are inserted into a drive for transfer onto another computer-readable storage medium that is also part of persistent storage 708.

Communications unit 712, in these examples, provides for communications with other data processing systems or devices. In these examples, communications unit 712 includes one or more network interface cards. Communications unit 712 may provide communications through the use of either or both physical and wireless communications links. The programs thought mapping program 154 in server 150, brain mapping program 122 in brain mapping device 120, language processing program 132 in language processing device 130, and user interface 142 stored in user device 140 may be downloaded to persistent storage 708 through communications unit 712.

I/O interface(s) 714 allows for input and output of data with other devices that may be connected to server 150, neural monitor device 110, brain mapping device 120, language processing device 130, and user device 140. For example, I/O interface 714 may provide a connection to external devices 720 such as a keyboard, keypad, a touch screen, and/or some other suitable input device. External devices 720 can also include portable computer-readable storage media such as, for example, thumb drives, portable optical or magnetic disks, and memory cards. Software and data used to practice embodiments of the present invention, e.g., the programs thought mapping program 154 in server 150, brain mapping program 122 in brain mapping device 120, language processing program 132 in language processing device 130, and user interface 142 stored in user device 140, can be stored on such portable computer-readable storage media and can be loaded onto persistent storage 708 via I/O interface(s) 714. I/O interface(s) 714 can also connect to a display 722.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
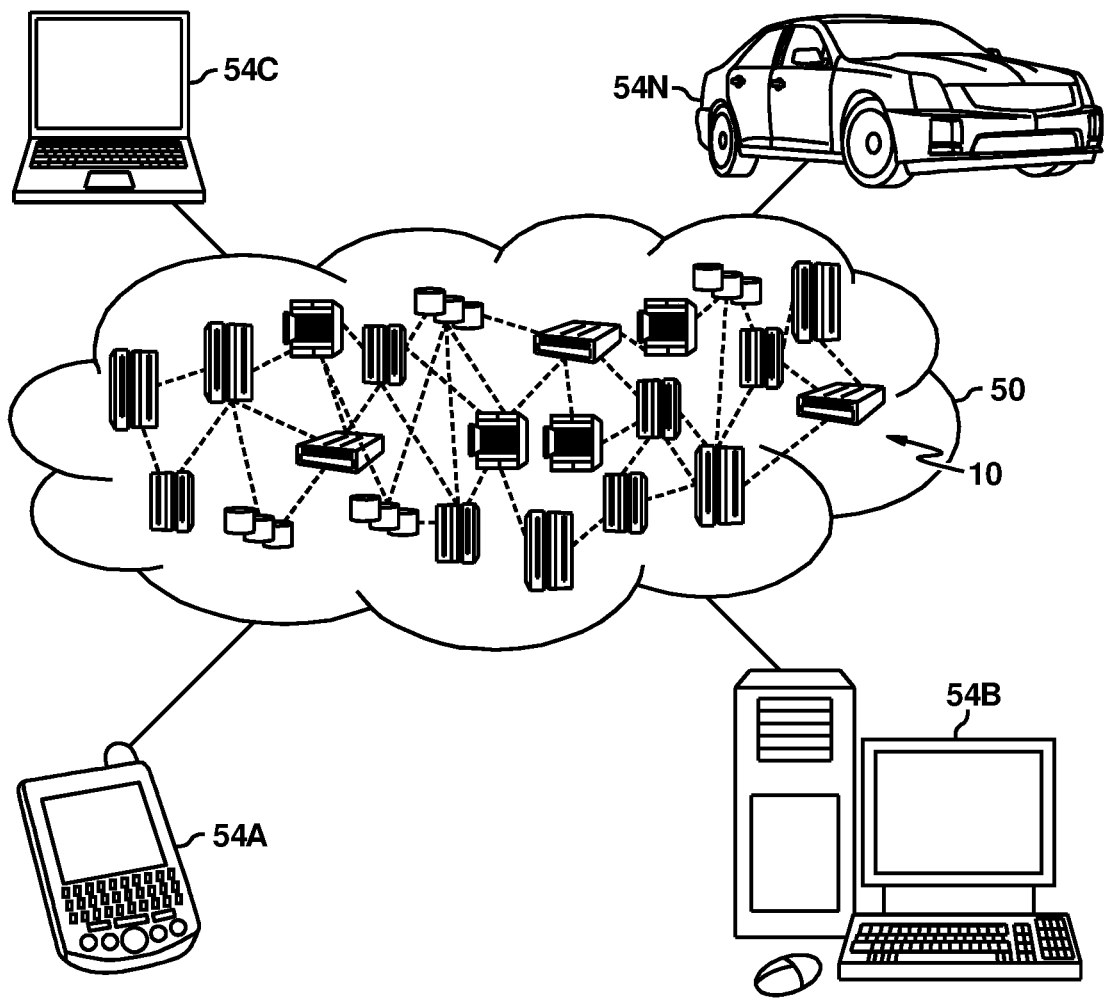
FIG. 5 illustrated a cloud computing environment, in accordance with an embodiment of the invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
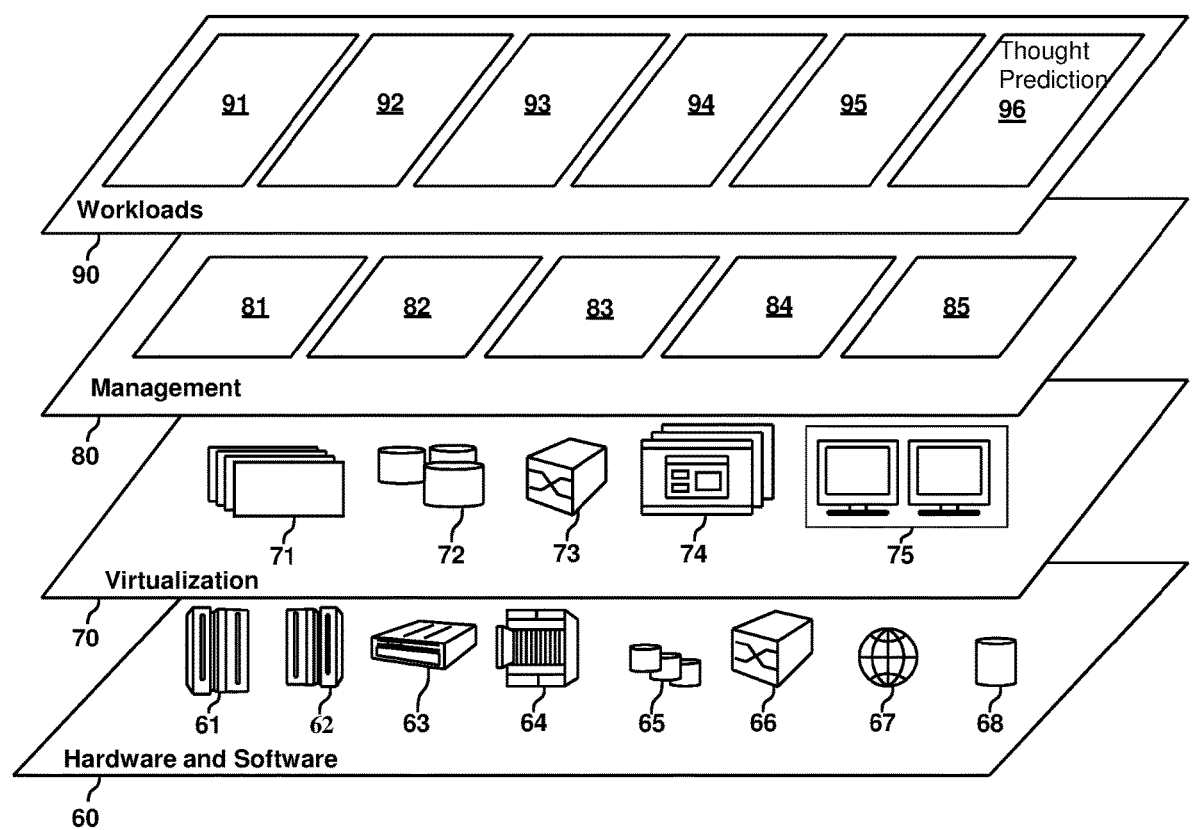
FIG. 6 illustrates a set of functional abstraction layers provided by the cloud computing environment of FIG. 5, in accordance with an embodiment of the invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and thought prediction 96.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

What is claimed is:

1. A computer program product for neural activity interpretation, the computer program product comprising:
    a computer-readable storage device and program instructions stored on computer-readable storage device, the program instructions comprising:
        program instructions to present a first user with a stimulus;
        program instructions to monitor neural activity of the first user;
        program instructions to map the neural activity of the first user;
        program instructions to receive the first user's verbal reaction to the stimulus;
        program instructions to map the linguistic data of the first user's verbal reaction;
        program instructions to form a high dimensional vector based on the relationships of the mapped neural activity of the first user and the mapped verbal reaction of the first user;
        program instructions to associate the high dimensional vector with the stimulus presented, resulting in a thoughts model; and
        program instructions to receive a second user neural activity (SUNA);
        program instructions to compare SUNA to the thoughts model to identify the neural activity in the second user.

2. The computer program product of claim 1, further comprising:
    program instructions to communicate a representation of the SUNA to a third user wherein the representation is based on the associated high dimensional vector of similar neural activity in the first user.

3. The computer program product of claim 1, further comprising:
    program instructions to receive the second user's verbal reaction to the stimulus;
    program instructions to identify the differences and similarities between the identified neural activity of the first user and the second user;
    program instructions to calibrate the parameters of the high dimensional vector to the SUNA.

4. The computer program product of claim 1, wherein the first user is capable of verbal communication.

5. The computer program product of claim 1, wherein the neural activity comprises electrical signals obtained from an electroencephalogram (EEG).

6. The computer program product of claim 1, wherein the stimulus is presented to the user in a virtual reality environment.

7. The computer program product of claim 1, wherein the stimulus is selected from a plurality of stimuli specifically designed to elicit a particular emotional state, memory, sensory experience, cognitive state, psychological response, and judgement.

8. A computer system for neural activity interpretation, the computer system comprising:
    a processor, a computer-readable tangible storage device, and program instructions stored on computer-readable tangible storage device for execution by the processor, the program instructions comprising:
        program instructions to present a first user with a stimulus;
        program instructions to monitor neural activity of the first user;
        program instructions to map the neural activity of the first user;

program instructions to receive the first user's verbal reaction to the stimulus;

program instructions to map the linguistic data of the first user's verbal reaction;

program instructions to form a high dimensional vector based on the relationships of the mapped neural activity of the first user and the mapped verbal reaction of the first user;

program instructions to associate the high dimensional vector with the stimulus presented, resulting in a thoughts model; and program instructions to receive a second user neural activity (SUNA);

program instructions to compare SUNA to the thoughts model to identify the neural activity in the second user.

9. The computer system of claim 8, further comprising:
program instructions to communicate a representation of the SUNA to a third user wherein the representation is based on the associated high dimensional vector of similar neural activity in the first user.

10. The computer system of claim 8, further comprising:
program instructions to receive the second user's verbal reaction to the stimulus;
program instructions to identify the differences and similarities between the identified neural activity of the first user and the second user;
program instructions to calibrate the parameters of the high dimensional vector to the SUNA.

11. The computer system of claim 8, wherein the stimulus is selected from a plurality of stimuli specifically designed to elicit a particular emotional state, memory, sensory experience, cognitive state, psychological response, and judgement.

* * * * *